US007816555B2

(12) United States Patent
Smith et al.

(10) Patent No.: US 7,816,555 B2
(45) Date of Patent: Oct. 19, 2010

(54) PEROXYCARBOXYLIC ACID COMPOSITIONS WITH REDUCED ODOR

(75) Inventors: Kim R. Smith, Woodbury, MN (US); Robert D. Hei, Baldwin, WI (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 12/562,695

(22) Filed: Sep. 18, 2009

(65) Prior Publication Data

US 2010/0022644 A1 Jan. 28, 2010

Related U.S. Application Data

(62) Division of application No. 10/346,862, filed on Jan. 17, 2003, now Pat. No. 7,622,606.

(51) Int. Cl.
*C07C 409/24* (2006.01)

(52) U.S. Cl. .............................................. 562/2; 562/3

(58) Field of Classification Search ........................ None
See application file for complete search history.

(56) References Cited

U.S. PATENT DOCUMENTS

| | | | |
|---|---|---|---|
| 2,512,640 A | 6/1950 | Greenspan et al. |
| 3,122,417 A | 2/1964 | Blaser et al. |
| 3,248,281 A | 4/1966 | Goodenough |
| 3,350,265 A | 10/1967 | Rubinstein et al. |
| 3,514,278 A | 5/1970 | Brink |
| 3,895,116 A | 7/1975 | Herting et al. |
| 3,996,386 A | 12/1976 | Malkki et al. |
| 4,041,149 A | 8/1977 | Gaffar et al. |
| 4,051,058 A | 9/1977 | Böwing et al. |
| 4,051,059 A | 9/1977 | Böwing et al. |
| 4,129,517 A | 12/1978 | Eggensperger et al. |
| 4,191,660 A | 3/1980 | Schreiber et al. |
| 4,244,884 A | 1/1981 | Hutchins et al. |
| 4,370,199 A | 1/1983 | Orndorff |
| 4,404,040 A | 9/1983 | Wang |
| 4,477,438 A | 10/1984 | Willcockson et al. |
| 4,478,683 A | 10/1984 | Orndorff |
| 4,501,681 A | 2/1985 | Groult et al. |
| 4,529,534 A | 7/1985 | Richardson |
| 4,557,898 A | 12/1985 | Greene et al. |
| 4,592,488 A | 6/1986 | Simon et al. |
| 4,613,452 A | 9/1986 | Sanderson |
| 4,655,781 A | 4/1987 | Hsieh et al. |
| 4,666,622 A | 5/1987 | Martin et al. |
| 4,715,980 A | 12/1987 | Lopes et al. |
| 4,738,840 A | 4/1988 | Simon et al. |
| 4,802,994 A | 2/1989 | Mouché et al. |
| 4,865,752 A | 9/1989 | Jacobs |
| 4,900,721 A | 2/1990 | Bansemir et al. |
| 4,906,617 A | 3/1990 | Jacquet et al. |
| 4,908,306 A | 3/1990 | Lorincz |
| 4,917,815 A | 4/1990 | Beilfuss et al. |
| 4,923,677 A | 5/1990 | Simon et al. |
| 4,937,066 A | 6/1990 | Vlock |
| 4,943,414 A | 7/1990 | Jacobs et al. |
| 4,945,110 A | 7/1990 | Brokken et al. |
| 4,996,062 A | 2/1991 | Lehtonen et al. |
| 4,997,571 A | 3/1991 | Roensch et al. |
| 4,997,625 A | 3/1991 | Simon et al. |
| 5,004,760 A | 4/1991 | Patton et al. |
| 5,010,109 A | 4/1991 | Inoi |
| 5,015,408 A | 5/1991 | Reuss |
| 5,043,176 A | 8/1991 | Bycroft et al. |
| 5,069,286 A | 12/1991 | Roensch et al. |
| 5,078,896 A | 1/1992 | Rorig et al. |
| 5,084,239 A | 1/1992 | Moulton et al. |
| 5,093,140 A | 3/1992 | Watanabe |
| 5,114,178 A | 5/1992 | Baxter |
| 5,114,718 A | 5/1992 | Damani |
| 5,122,538 A | 6/1992 | Lokkesmoe et al. |
| 5,129,824 A | 7/1992 | Keller |
| 5,130,124 A | 7/1992 | Merianos et al. |
| 5,139,788 A | 8/1992 | Schmidt |
| 5,176,899 A | 1/1993 | Montgomery |
| 5,200,189 A | 4/1993 | Oakes et al. |
| 5,208,057 A | 5/1993 | Greenley et al. |
| 5,234,703 A | 8/1993 | Guthery |
| 5,234,719 A | 8/1993 | Richter et al. |

(Continued)

FOREIGN PATENT DOCUMENTS

| | | |
|---|---|---|
| CA | 2181416 | 7/1996 |
| DE | 1 494 109 | 12/1973 |
| DE | 35 43 500 A1 | 6/1987 |
| DE | 39 06 044 A1 | 8/1990 |
| DE | 197 51 391 A1 | 7/1998 |
| EP | 0 195 619 A2 | 9/1986 |
| EP | 0 233 731 A2 | 8/1987 |
| EP | 0 404 293 A2 | 3/1990 |
| EP | 0 461 700 A1 | 12/1991 |
| EP | 0 569 066 A1 | 11/1993 |
| EP | 0 667 392 A2 | 2/1995 |

(Continued)

OTHER PUBLICATIONS

Armak Chemicals, "NEO-FAT Fatty Acids", *Akzo Chemicals Inc.*, Bulletin No. 86-17 (1986).

(Continued)

*Primary Examiner*—Karl J Puttlitz
(74) *Attorney, Agent, or Firm*—Andrew D. Sorensen; Laura C. Dilorenzo

(57) ABSTRACT

The present invention relates to compositions of peroxycarboxylic acid that have reduced odor compared to conventional peroxycarboxylic acid compositions, methods employing these reduced-odor compositions, and methods of making these compositions. Typically, the reduced-odor compositions include an amine oxide surfactant.

16 Claims, No Drawings

U.S. PATENT DOCUMENTS

| | | | |
|---|---|---|---|
| 5,268,003 A | 12/1993 | Coope et al. |
| 5,292,447 A | 3/1994 | Venturello et al. |
| 5,292,955 A | 3/1994 | Smith et al. |
| 5,314,687 A | 5/1994 | Oakes et al. |
| 5,336,500 A | 8/1994 | Richter et al. |
| 5,364,650 A | 11/1994 | Guthery |
| 5,391,324 A | 2/1995 | Reinhardt et al. |
| 5,409,713 A | 4/1995 | Lokkesmoe et al. |
| 5,419,908 A | 5/1995 | Richter et al. |
| 5,435,808 A | 7/1995 | Holzhauer et al. |
| 5,436,008 A | 7/1995 | Richter et al. |
| 5,437,868 A | 8/1995 | Oakes et al. |
| 5,489,434 A | 2/1996 | Oakes et al. |
| 5,494,588 A | 2/1996 | LaZonby |
| 5,508,046 A | 4/1996 | Cosentino et al. |
| 5,512,309 A | 4/1996 | Bender et al. |
| 5,578,134 A | 11/1996 | Lentsch et al. |
| 5,591,706 A | 1/1997 | Ploumen |
| 5,595,967 A | 1/1997 | Miracle et al. |
| 5,597,790 A | 1/1997 | Thoen |
| 5,616,335 A | 4/1997 | Nicolle et al. |
| 5,616,616 A | 4/1997 | Hall et al. |
| 5,632,676 A | 5/1997 | Kurschner et al. |
| 5,641,530 A | 6/1997 | Chen |
| 5,656,302 A | 8/1997 | Cosentino et al. |
| 5,658,467 A | 8/1997 | LaZonby et al. |
| 5,674,538 A | 10/1997 | Lokkesmoe et al. |
| 5,674,828 A | 10/1997 | Knowlton et al. |
| 5,683,724 A | 11/1997 | Hei et al. |
| 5,712,239 A | 1/1998 | Knowlton et al. |
| 5,718,910 A | 2/1998 | Oakes et al. |
| 5,756,139 A | 5/1998 | Harvey et al. |
| 5,770,551 A | 6/1998 | Block et al. |
| 5,785,867 A | 7/1998 | LaZonby et al. |
| 5,827,542 A | 10/1998 | Miner et al. |
| 5,840,343 A | 11/1998 | Hall et al. |
| 5,851,483 A | 12/1998 | Nicolle et al. |
| 5,891,392 A | 4/1999 | Monticello et al. |
| 5,900,256 A | 5/1999 | Scoville, Jr. et al. |
| 5,902,619 A | 5/1999 | Rubow et al. |
| 5,962,392 A | 10/1999 | Revell et al. |
| 5,968,539 A | 10/1999 | Beerse et al. |
| 5,989,611 A | 11/1999 | Stemmler, Jr. et al. |
| 5,998,358 A | 12/1999 | Herdt et al. |
| 6,010,729 A | 1/2000 | Gutzmann et al. |
| 6,024,986 A | 2/2000 | Hei |
| 6,033,705 A | 3/2000 | Isaacs |
| 6,049,002 A | 4/2000 | Mattila et al. |
| 6,080,712 A | 6/2000 | Revell et al. |
| 6,096,226 A | 8/2000 | Fuchs et al. |
| 6,096,266 A | 8/2000 | Duroselle |
| 6,096,348 A | 8/2000 | Miner et al. |
| 6,096,349 A | 8/2000 | Petri et al. |
| 6,168,808 B1 | 1/2001 | Godin et al. |
| 6,369,288 B1 | 4/2002 | Brown |
| 6,444,230 B1 | 9/2002 | Godin et al. |
| 6,479,454 B1 | 11/2002 | Smith et al. |
| 6,627,593 B2 * | 9/2003 | Hei et al. ............ 510/375 |
| 6,630,435 B1 | 10/2003 | Gagliardini et al. |

FOREIGN PATENT DOCUMENTS

| | | |
|---|---|---|
| EP | 0 779 357 A1 | 12/1995 |
| EP | 0 805 198 A1 | 7/1996 |
| EP | 0 843 001 A1 | 11/1996 |
| EP | 0 985 349 A2 | 3/2000 |
| FR | 2 321 301 A | 3/1977 |
| FR | 2 324 626 A | 4/1977 |
| GB | 2 255 507 A | 5/1991 |
| LU | 78 568 A | 4/1978 |
| RU | 2102447 | 8/1996 |
| WO | WO 93/01716 | 2/1993 |
| WO | WO 93/03006 | 2/1993 |
| WO | WO 94/21122 | 9/1994 |
| WO | WO 94/23575 | 10/1994 |
| WO | WO 95/34537 | 12/1995 |
| WO | WO 96/30474 | 3/1996 |
| WO | WO 98/28267 | 7/1998 |
| WO | WO 99/51095 | 10/1999 |

OTHER PUBLICATIONS

Bell, K. et al., "Reduction of foodborne micro-organisms on beef carcass tissue using acetic acid, sodium bicarbonate, and hydrogen peroxide spray washes", *Food Microbiology*, vol. 14, pp. 439-448 (1997).

Computer search results—Level 1—5 patents (Mar. 1994).

Computer search results from Ecolab Information Center (Jun. 1998).

International Search Report dated Aug. 5, 2004.

International Search Report dated Jan. 30, 2002 (10 pages).

Eggensperger, H., "Disinfectants Based on Peracid-Splitting Compounds", *Zbl. Bakt. Hyg.*, I. Abt. Orig. B 168, pp. 517-524 (1979).

"Emery® Fatty and Dibasic Acids Specifications and Characteristics", *Emery Industries*, Bulletin 145, (Oct. 1983).

"Indirect food additives: adjuvants, production aids, and sanitizers", Fed. Regist., vol. 61, No. 108, pp. 28051-28053 (Jun. 4, 1996) (abstract only).

Lion C. et al., "New decontaminants. Reaction of peroxyacid esters with toxic insecticides", *Bull. Soc. Chim. Belg.*, vol. 100, No. 7, pp. 555-559 (1991).

Merka, V. et al., "Disinfectant properties of some peroxide compounds.", Abstract No. 67542e, *Chemical Abstracts*, vol. 67 (1967).

Mulder, R.W.A.W. et al., "Research Note: Salmonella Decontamination of Broiler Carcasses with Lactic Acid, L-Cysteine, and Hdrogen Peroxide", *Poultry Science*, vol. 66, pp. 1555-1557 (1987).

Parker, W. et al., "Peroxides. IV. Aliphatic Diperacids", *Aliphatic Diperacids*, vol. 79, pp. 1929-1931 (Apr. 20, 1957).

Parker, W. et al., "Peroxides. II. Preparation, Characterization and Polarographic Behavior of Longchaing Aliphatic Peracids", *Synthesis and Properties of LongChain Aliphatic Peracids*, vol. 77, pp. 4037-4041 (Aug. 5, 1955).

Pfizer Chemical Division, "Pfizer Flocon® Biopolymers for Industrial Uses (xanthan broths)", Data Sheet 679, pp. 1-4 (year unknown).

Search Report for the use of Amine Oxides Used with Hydrogen Peroxide.

Search Report for the use of amine oxides with hydrogen peroxide in bleaching, sanitizing, disinfectant or hard surface cleaners, dated Nov. 12, 1998.

Search Result from Database WPI and Database INPADOC.

Towle, G. et al., "Industrial Gums polysaccharides and Their Derivatives", Second Edition, Ch. XIX, "Pectin", pp. 429-444 (year unknown).

* cited by examiner

PEROXYCARBOXYLIC ACID COMPOSITIONS WITH REDUCED ODOR

CROSS REFERENCE TO RELATED APPLICATION

This is a divisional application of U.S. application Ser. No. 10/346,862, filed Jan. 17, 2003, published as US 2004-0143133, now issued as U.S. Pat. No. 7,622,606 on Nov. 24, 2009. The entire disclosure of which is incorporated herein by reference in its entirety.

FIELD OF THE INVENTION

The present invention relates to compositions of peroxycarboxylic acid that have reduced odor compared to conventional peroxycarboxylic acid compositions, methods employing these reduced-odor compositions, and methods of making these compositions. Typically, the reduced-odor compositions include an amine oxide surfactant.

BACKGROUND OF THE INVENTION

Peroxycarboxylic acid compositions exhibit useful antimicrobial activity. Many existing compositions including peroxycarboxylic acids suffer from unacceptable odor.

SUMMARY OF THE INVENTION

The present invention relates to compositions of peroxycarboxylic acid that have reduced odor compared to conventional peroxycarboxylic acid compositions, methods employing these reduced-odor compositions, and methods of making these compositions. Typically, the reduced-odor compositions include an amine oxide surfactant.

The present invention includes a composition including a peroxycarboxylic acid and an amine oxide surfactant. The composition can be in the form of a concentrate or a dilute use composition. The concentrate composition can include 0.1 to 40 wt-% amine oxide and 0.1 to 40 wt-% peroxycarboxylic acid, with a mole ratio of amine oxide to peroxycarboxylic acid of 1 or more. The composition of the invention has reduced odor of peroxycarboxylic acid compared to a composition lacking the amine oxide. The composition can also include other components, such as one or more carboxylic acids, one or more surfactants, one or more hydrotropes, one or more coupling agents, one or more solubilizers, one or more chelating agents, or the like.

The concentrate composition can be diluted in a major proportion of an aqueous fluid to form an antimicrobial use composition. A use composition can include peroxycarboxylic acid at 10 to 10,000 ppm and amine oxide of 10 to 10,000 ppm, with a mole ratio of amine oxide to peroxycarboxylic acid of 1 or more. The composition of the invention has reduced odor of peroxycarboxylic acid compared to a composition lacking the amine oxide. The use composition can also include other components, such as one or more carboxylic acids, one or more surfactants, one or more hydrotropes, one or more coupling agents, one or more solubilizers, one or more chelating agents, or the like.

In another embodiment, the invention includes a method employing the reduced-odor composition of the invention to reduce a population of one or more microorganisms on an object, such as on a surface or in a fluid. In an embodiment, the invention includes a method employing the reduced-odor composition of the invention to reduce the population of a microorganism on skin or to treat a disease of skin. In an embodiment, the invention includes a method employing the reduced-odor composition of the invention to reduce an odor of an object, such as of a surface or of a fluid. In an embodiment, the invention includes a method employing the reduced-odor composition of the invention to bleach an object. These methods include contacting the object with a reduced-odor peroxycarboxylic acid composition of the invention. Contacting can include spraying the composition, immersing the object in the composition, foam or gel treating the object with the composition, or a combination thereof.

DETAILED DESCRIPTION OF THE INVENTION

The present invention relates to antimicrobial compositions including an effective antimicrobial amount of an amine oxide and peroxycarboxylic acid, with a mole ratio of amine oxide to peroxycarboxylic acid of 1 or more. The composition of the invention has reduced odor of peroxycarboxylic acid compared to a composition lacking the amine oxide. The present reduced-odor antimicrobial composition can be used effectively to reduce the microbial population of hard surfaces such as those in facilities and equipment used in the food and beverage industries. Additionally, the present composition can be used to effectively reduce the microbial population of food, of dishware, and to treat water.

DEFINITIONS

As used herein, the term "microorganisms" refers to any noncellular or unicellular (including colonial) organism. Microorganisms include all prokaryotes. Microorganisms include bacteria (including cyanobacteria), lichens, microfungi, protozoa, virinos, viroids, viruses, and some algae. As used herein, the term "microbe" is synonymous with microorganism.

As used herein, the term "object" refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors.

As used herein, the phrase "food product" includes any food substance that might require treatment with an antimicrobial agent or composition and that is edible with or without further preparation. Food products include meat (e.g. red meat and pork), seafood, poultry, fruits and vegetables, eggs, living eggs, egg products, ready to eat food, wheat, seeds, roots, tubers, leafs, stems, corms, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydro-cooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein, the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and handwash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or woven and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a reduced-odor composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, arthoscopes and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, weight percent (wt-%), percent by weight, % by weight, and the like are synonyms that refer to the concentration of a substance as the weight of that substance divided by the weight of the composition and multiplied by 100.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

For the purpose of this patent application, successful reduction of microorganisms is achieved when the populations of microorganisms are reduced by at least about 0.3-1 $\log_{10}$. In this application, such a population reduction is the minimum acceptable for the processes. Any increased reduction in population of microorganisms is an added benefit that provides higher levels of protection.

Reduced-Odor Peroxycarboxylic Acid Compositions

The present invention relates to reduced-odor compositions containing a peroxycarboxylic acid. Typically, the reduced-odor compositions also include an amine oxide at a mole ratio of amine oxide to peroxycarboxylic acid of 1 or more. Typically, the peroxycarboxylic acid is an antimicrobial agent. Many peroxycarboxylic acid composition exhibit a sharp, annoying, or otherwise unacceptable odor. Surprisingly, such an unacceptable odor can be reduced by adding an amine oxide to the peroxycarboxylic acid. The present composition of the invention has reduced odor of peroxycarboxylic acid compared to a composition lacking the amine oxide.

The peroxycarboxylic acid can be made in the presence of the amine oxide, or the amine oxide can be added after forming the peroxycarboxylic acid. In an embodiment, the amine oxide can be employed in food products or for cleaning or sanitizing food processing equipment or materials. In an embodiment, the amine oxide can be employed in a health care environment. In an embodiment, the amine oxide is non-toxic. In an embodiment, the amine oxide can be employed according to guidelines from government agencies, such as the Food and Drug Administration, without adverse labeling requirements, such as labeling with a skull and cross bones or the like. Preferred amine oxides include octyl amine oxide (e.g., octyldimethylamine oxide), lauryldimethyl amine oxide, and the like.

The amine oxide is typically present in a quantity that effectively reduces odor of the peroxycarboxylic acid. Suitable levels of amine oxide include a mole ratio of amine oxide to peroxycarboxylic acid of 1 or more. In an embodiment, the mole ratio is greater than or equal to 2. In an embodiment, the mole ratio is greater than or equal to 3. In an embodiment, the mole ratio is 2 to 5. In an embodiment, the mole ratio is 3 to 5. Octyl dimethyl amine oxide has a molecular weight of about 3 (e.g. 2.7) times as great as peroxyacetic acid, and applicable weight ratios can be calculated on such a basis.

In an embodiment, the composition includes about 15 to about 60 wt-% amine oxide. In an embodiment, the composition includes about 30 to about 50 wt-% amine oxide. In an embodiment, the composition includes about 45 wt-% amine oxide.

Amine Oxides

Examples of suitable amine oxides include those having a general formula of

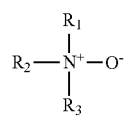

wherein $R_1$, $R_2$, and $R_3$ are independently selected from saturated or unsaturated and straight or branched alkyl groups having from 1-24 carbons and aromatic groups, etc. and which can optionally contain O, N or P as a heteroatom or polyalkoxy groups. Examples of amine oxides include, but are not limited to: alkyldimethylamine oxide, dialkylmethylamine oxide, alkyldialkoxylamine oxide, dialkylalkoxyamine oxide, dialkyletheramine oxide and dialkoxyetheramine oxide. In an embodiment, $R_1$ is an alkyl group having 4-18 carbons and $R_2$ and $R_3$ are alkyl groups having 1-18 carbons. In an embodiment, $R_1$ is an alkyl group having 6-10 carbons and $R_2$ and $R_3$ are alkyl groups having 1-2 carbons. In an embodiment, $R_1$ is an alkyl group having 8 carbons (an octyl group) and $R_2$ and $R_3$ are alkyl groups having 1-2 carbons. In an embodiment, $R_1$ is an alkyl group having 12 carbons (a lauryl group) and $R_2$ and $R_3$ are alkyl groups having 1-2 carbons.

Preferred amine oxides include octyldimethylamine oxide, myristyldimethylamine oxide, didecylmethylamine oxide, methylmorpholine oxide, tetradecyldiethoxyamine oxide, and lauryldimethylamine oxide. Preferred amine oxides include octyldimethylamine oxide and lauryldimethylamine oxide.

Peroxycarboxylic Acids

Peroxycarboxylic (or percarboxylic) acids generally have the formula $R(CO_3H)_n$, where R is an alkyl, arylalkyl, cycloalkyl, aromatic, heterocyclic, or ester group, such as an alkyl ester group; and n is one, two, or three, and named by prefixing the parent acid with peroxy. Ester groups are defined as R groups including organic moieties (such as those listed above for R) and ester moieties. Preferred ester groups include aliphatic ester groups, such as $R_1OC(O)R_2$— where each of $R_1$ and $R_2$ can be aliphatic, preferably alkyl, groups described above for R. Preferably $R_1$ and $R_2$ are each independently small alkyl groups, such as alkyl groups with 1 to 5 carbon atoms.

While peroxycarboxylic acids are not as stable as carboxylic acids, their stability generally increases with increasing molecular weight. Thermal decomposition of these acids can generally proceed by free radical and nonradical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxycitric, peroxymaleic, peroxyascorbic, peroxyhydroxyacetic (peroxyglycolic), peroxyoxalic, peroxymalonic, peroxysuccinic, peroxyglutaric, peroxyadipic, peroxypimelic, peroxysuberic, and peroxysebacic acid, and mixtures thereof. Useful peroxycarboxylic acids also include the ester peroxycarboxylic acids described herein and compositions of the present invention including those ester peroxycarboxylic acids.

Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids.

In a preferred embodiment, the composition of the invention utilizes a combination of several different peroxycarboxylic acids. Preferably, the composition includes one or more small $C_2$-$C_4$ peroxycarboxylic acids, one or more large $C_8$-$C_{12}$ peroxycarboxylic acids, and/or one or more alkyl ester peroxycarboxylic acid compositions. Especially preferred is an embodiment in which the small peroxycarboxylic acid is peroxyacetic acid and the large acid is either peroxyoctanoic acid or peroxydecanoic acid.

Ester Peroxycarboxylic Acids

As used herein, ester peroxycarboxylic acid refers to a molecule having the formula:

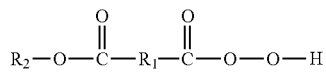

In this formula, $R_1$ and $R_2$ can independently be any of a wide variety of organic groups (e.g. alkyl, linear or cyclic, aromatic or saturated) or substituted organic groups (e.g., with one or more heteroatoms or organic groups). Ester peroxycarboxylic acid can be made using methods typically employed for producing peroxycarboxylic acid, such as incubating the corresponding ester carboxylic acid with hydrogen peroxide.

Preferred ester peroxycarboxylic acids include alkyl ester peroxycarboxylic acids, preferably having the formula:

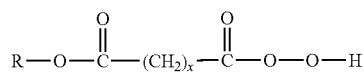

where R represents an alkyl group having from 1 to 4 carbons and x is 0 to 5, preferably 1 to 4. The alkyl group can be either straight chain or branched. Preferably, R is a methyl, ethyl, propyl, or isobutyl group. Preferably, x is 2, 3, or 4.

In one preferred embodiment, the composition of the present invention includes a mixture of alkyl ester peroxycarboxylic acids in which x is 2, 3, and 4. Such a mixture includes monoesters of peroxyadipic, peroxyglutaric, and peroxysuccinic acids. In another preferred embodiment, a majority of the ester peroxycarboxylic acid in the composition has x equal to 3. In a preferred embodiment, R is a $C_1$-$C_4$ alkyl. In a preferred embodiment, x is 1, 2, 3, or 4. Most preferably, R is a $C_1$ alkyl, $C_3$ alkyl, or $C_4$ alkyl, and x is 2, 3 or 4.

In another preferred embodiment, R represents an alkyl group having from 1 to 8 carbons, and x is 0 to 10. The alkyl group can be either straight chain or branched, preferably straight chain. In this embodiment, preferably x is 4-8 and R is $C_1$ to $C_4$ alkyl, preferably methyl or ethyl.

Alkyl ester peroxycarboxylic acids useful in this invention include monomethyl monoperoxyoxalic acid, monomethyl monoperoxymalonic acid, monomethyl monoperoxysuccinic acid, monomethyl monoperoxyglutaric acid, monomethyl monoperoxyadipic acid, monomethyl monoperoxypimelic acid, monomethyl monoperoxysuberic acid, and monomethyl monoperoxysebacic acid; monoethyl monoperoxyoxalic acid, monoethyl monoperoxymalonic acid, monoethyl monoperoxysuccinic acid, monoethyl monoperoxyglutaric acid, monoethyl monoperoxyadipic acid, monoethyl monoperoxypimelic acid, monoethyl monoperoxysuberic acid, and monoethyl monoperoxysebacic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, monopropyl monoperoxypimelic acid, monopropyl monoperoxysuberic acid, and monopropyl monoperoxysebacic acid, in which propyl can be n- or isopropyl; and monobutyl monoperoxyoxalic acid, monobutyl monoperoxymalonic acid, monobutyl monoperoxysuccinic acid, monobutyl monoperoxyglutaric acid, monobutyl monoperoxyadipic acid, monobutyl monoperoxypimelic acid, monobutyl monoperoxysuberic acid, and monobutyl monoperoxysebacic acid, in which butyl can be n-, iso-, or t-butyl.

In a preferred embodiment, the antimicrobial composition includes one or more alkyl ester peroxycarboxylic acids and a peroxycarboxylic acid having from 2 to 12 carbon atoms. Preferably, such an antimicrobial composition includes peroxyacetic acid, or peroxyoctanoic acid, or peroxydecanoic acid, and monomethyl monoperoxyoxalic acid, monomethyl monoperoxymalonic acid, monomethyl monoperoxysuccinic acid, monomethyl monoperoxyglutaric acid, monomethyl monoperoxyadipic acid, monomethyl monoperoxypimelic acid, monomethyl monoperoxysuberic acid, or monomethyl monoperoxysebacic acid; monoethyl monoperoxyoxalic acid, monoethyl monoperoxymalonic acid, monoethyl monoperoxysuccinic acid, monoethyl monoperoxyglutaric acid, monoethyl monoperoxyadipic acid, monoethyl monoperoxypimelic acid, monoethyl monoperoxysuberic acid, or monoethyl monoperoxysebacic acid; monopropyl monoperoxyoxalic acid, monopropyl monoperoxymalonic acid, monopropyl monoperoxysuccinic acid, monopropyl monoperoxyglutaric acid, monopropyl monoperoxyadipic acid, monopropyl monoperoxypimelic acid, monopropyl monoperoxysuberic acid, or monopropyl monoperoxysebacic acid, in which propyl can be n- or isopropyl; or monobutyl monoperoxyoxalic acid, monobutyl monoperoxymalonic acid, monobutyl monoperoxysuccinic acid, monobutyl monoperoxyglutaric acid, monobutyl monoperoxyadipic acid, monobutyl monoperoxypimelic acid, monobutyl monoperoxysuberic acid, or monobutyl monoperoxysebacic acid, in which butyl can be n-, iso-, or t-butyl, or mixtures thereof. Preferably, in such mixtures the alkyl ester peroxycarboxylic acid is one of the above, and the peroxycarboxylic acid having from 2 to 12 carbon atoms is peroxyacetic acid or peroxyoctanoic acid; combined in a ratio of about 1 to about 10 parts by weight of peroxyacetic acid per each 1 part of carboxylic acid. In another embodiment, when a blended acid is used, the peroxycarboxylic acids are blended in proportions that range from about 1 part to about 20 parts by weight of alkyl ester peroxyacid to mono- or di-peroxycarboxylic acid having up to 12 carbon atoms. In another preferred embodiment, the combination of peroxycarboxylic acid includes an alkyl ester peroxyacid and a mono- or di-peroxycarboxylic acid having up to 12 carbon atoms.

The amount of alkyl ester peroxycarboxylic acid in use and concentrate compositions can range up to the limits at which the peroxycarboxylic acid can be dissolved or suspended in the composition. Preferably, the alkyl ester peroxycarboxylic acid is present in a use or concentrate composition at a concentration of from about 0.0001 to about 20% by weight, preferably from about 0.05 to about 15% by weight, and more preferably from about 4 to about 10% by weight. Typically use compositions include at least 0.1%, preferably at least 1%, by weight alkyl ester peroxycarboxylic acid.

Reduced-odor compositions of ester peroxycarboxylic acid can also include other ingredients, for example, to increase solubility of the ester peroxycarboxylic acid or to maintain the pH of the composition. Preferably the reduced-odor composition includes a surfactant. It is believed that the surfactant can increase the solubility of the ester peroxycarboxylic acid. Suitable surfactants include nonionic surfactants, anionic surfactants, cationic surfactants, amphoteric surfactants, and the like. Preferred surfactants include alkylbenzene sulfonic acids and their salts, alkyl sulfonates, straight-chain or branched alcohol ethoxylates, amine oxides, and the like. Preferably the surfactant is present at about 0 to about 15 wt-% of the composition, preferably about 0 to about 10 wt-%, and most preferably about 0 to about 8 wt-%.

Preferably the reduced-odor composition includes a buffer. Preferred buffers maintain the pH of the composition, after dilution to the use concentration, below about 7, preferably below about 5, and more preferably below about 4. Preferred buffers include citric acid and its salts, phosphoric acid and its salts, succinic acid and its salts, adipic acid and its salts, glutaric acid and its salts, acetic acid and its salts, boric acid and its salts, and mixtures thereof. Preferably the buffer is present at about 0 to about 20 wt-% of the composition, preferably about 0 to about 10 wt-%, and most preferably about 0 to about 7 wt-%.

The reduced-odor compositions of the invention can be formulated as a liquid, a gel, an aerosol, a gas, a wax, a solid, or a powder, or as a solution or suspension containing such a composition.

Compositions of Peroxycarboxylic Acids

A preferred antimicrobial reduced-odor peroxycarboxylic acid composition of the present invention is effective for killing one or more of the food-borne pathogenic bacteria associated with a food product, such as *Salmonella typhimurium, Salmonella javiana, Campylobacter jejuni, Listeria monocytogenes*, and *Escherichia coli* O157:H7, yeast, mold and the like. The compositions and methods of the present invention have activity against a wide variety of microorganisms such as Gram positive (for example, *Listeria monocytogenes*) and Gram negative (for example, *Escherichia coli*) bacteria, yeast, molds, bacterial spores, viruses, etc. The compositions and methods of the present invention, as described above, have activity against a wide variety of human pathogens. The compositions and methods can kill a wide variety of microorganisms on a food processing surface, on the surface of a food product, or in water used for washing or processing of food product.

A preferred antimicrobial reduced-odor peroxycarboxylic acid composition of the present invention is effective for killing one or more of the pathogenic bacteria associated with a health care surfaces and environments, such as *Salmonella typhimurium, Staphylococcus aureus, Salmonella choleraesurus, Pseudomonas aeruginosa*, and *Escherichia coli*, mycobacteria, yeast, mold, and the like. The compositions and methods of the present invention have activity against a wide variety of microorganisms such as Gram positive (for example, *Staphylococcus aureus*) and Gram negative (for example, *Pseudomonas aeruginosa*) bacteria, yeast, molds, bacterial spores, viruses, etc. The compositions and methods of the present invention, as described above, have activity against a wide variety of human pathogens. The compositions and methods can kill a wide variety of microorganisms on a health care surface or in a health care environment.

The preferred compositions include concentrate compositions and use compositions. Typically, an antimicrobial concentrate composition can be diluted, for example with water, to form an antimicrobial use composition. In a preferred embodiment, the concentrate composition is diluted into water employed for washing or processing food product.

The advantageous stability of mixed peroxycarboxylic acid compositions in such methods, which include the presence of food product or health care debris or residue, makes these compositions competitive with cheaper, less stable, and potentially toxic chlorinated compounds. Preferred methods of the present invention include agitation or sonication of the use composition, particularly as a concentrate is added to water to make the use composition. Preferred methods include water systems that have some agitation, spraying, or other mixing of the solution.

The level of reactive species, such as peroxy acids and/or hydrogen peroxide, in a use composition can be affected, typically diminished, by organic matter that is found in or added to the use composition. For example, when the use composition is a bath or spray used for washing food product, food product organic matter or accompanying organic matter will consume peroxy acid and peroxide. Thus, the amounts of ingredients listed for the use compositions refer to the composition before or early in use, with the understanding that the amounts will diminish as organic matter is added to the use composition.

In addition, the concentrate and use compositions change with age. It is believed that in approximately one year at ambient conditions the amount of peroxycarboxylic acid in the compositions can decrease to about 50% to about 80%, preferably about 80% to about 85%, of the initial equilibrium values or use composition levels. Such aged compositions are included in the scope of the present invention.

In an embodiment, the compositions of the present invention preferably include only ingredients that can be employed in food products or in food product washing, handling, or processing, for example, according to government (e.g., FDA or USDA) rules and regulations. Preferably, the composition is free of any non-ester peroxycarboxylic acid or carboxylic acid with 10, 12, or more carbon atoms. Such non-ester 10, 12, or more carbon acids can impart undesirable residues (e.g., bad tasting and/or malodorous) to food product.

Each of the compositions listed above can be formulated by combining each of the listed ingredients. In addition, certain compositions including both acid and peroxy acid can be formulated by combining the acids and hydrogen peroxide, which forms peroxy acids. Typically, the pH of an equilibrium mixture is less than about 1 or about 2, and the pH of a 1% solution of the equilibrium mixture in water is about 2 to about 7, depending on the other components of the 1% solution, and the pH of a use composition can be from about 3 to about 7 depending on the other components.

Among other constituents, the composition of the present invention can include a carboxylic acid. Generally, carboxylic acids have the formula R—COOH wherein the R can represent any number of different groups including aliphatic groups, alicyclic groups, aromatic groups, heterocyclic groups, and ester groups, such as alkyl ester groups, all of which can be saturated or unsaturated and/or substituted or unsubstituted. Carboxylic acids can have one, two, three, or more carboxyl groups. Preferred ester groups include aliphatic ester groups, such as $R_1OC(O)R_2$— where each of $R_1$ and $R_2$ can be aliphatic, preferably alkyl, groups described above for R. Preferably $R_1$ and $R_2$ are each independently small alkyl groups, such as alkyl groups with 1 to 4 carbon atoms.

The composition and methods of the invention can employ carboxylic acids containing as many as 18 carbon atoms. Examples of suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic (glycolic), neopentanoic, neoheptanoic, neodecanoic, oxalic, malonic, succinic, glutaric, adipic, pimelic suberic, and sebacic acid. Examples of suitable alkyl ester carboxylic acids include monomethyl oxalic acid, monomethyl malonic acid, monomethyl succinic acid, monomethyl glutaric acid, monomethyl adipic acid, monomethyl pimelic acid, monomethyl suberic acid, and monomethyl sebacic acid; monoethyl oxalic acid, monoethyl malonic acid, monoethyl succinic acid, monoethyl glutaric acid, monoethyl adipic acid, monoethyl pimelic acid, monoethyl suberic acid, and monoethyl sebacic acid; monopropyl oxalic acid, monopropyl malonic acid, monopropyl succinic acid, monopropyl glutaric acid, monopropyl adipic acid, monopropyl pimelic acid, monopropyl suberic acid, and monopropyl sebacic acid, in which propyl can be n- or isopropyl; and monobutyl oxalic acid, monobutyl malonic acid, monobutyl succinic acid, monobutyl glutaric acid, monobutyl adipic acid, monobutyl pimelic acid, monobutyl suberic acid, and monobutyl sebacic acid, in which butyl can be n-, iso-, or t-butyl.

Carboxylic acids which are generally useful are those having one or two carboxyl groups where the R group is a primary alkyl chain having a length of $C_2$ to $C_{12}$. The primary alkyl chain is that carbon chain of the molecule having the greatest length of carbon atoms and directly appending carboxyl functional groups. Longer chain carboxylic acid analogs, including hexanoic, heptanoic, octanoic, nonanoic, and decanoic, can reduce surface tension to assist in wetting of hydrophobic surfaces like skin.

In a preferred embodiment, the antimicrobial composition includes one or more mono- or di-carboxylic acids having up to 18 carbon atoms. Preferred mono- or di-carboxylic acids having up to 18 carbon atoms include acetic acid, lactic acid, glycolic acid, citric acid, heptanoic acid, octanoic acid, nonanoic acid, or a mixture thereof. In another preferred embodiment, the antimicrobial composition includes an alpha-hydroxy mono- or di-carboxylic acid having from 3 to 6 carbon atoms, preferably lactic acid.

Carboxylic acids that are generally useful include ester carboxylic acids, such as alkyl ester carboxylic acids. Preferred alkyl ester carboxylic acids include those with the formula:

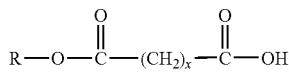

where R represents an alkyl group having from 1 to 4 carbons and x is 0 to 5, preferably 1 to 4. The alkyl group can be either straight chain or branched. Preferably, R is a methyl, ethyl, propyl, or isobutyl group. Preferably, x is 2, 3, or 4.

In one preferred embodiment, the composition of the present invention includes a mixture of alkyl ester peroxycarboxylic acids in which x is 2, 3, and 4. Such a mixture includes monoesters of peroxyadipic, peroxyglutaric, and peroxysuccinic acids. In another preferred embodiment, a majority of the ester peroxycarboxylic acid in the composition has x equal to 3. In a preferred embodiment, R is a $C_1$-$C_4$ alkyl. In a preferred embodiment, x is 1, 2, 3, or 4. Most preferably, R is a $C_1$ alkyl, $C_3$ alkyl, or $C_4$ alkyl, and x is 2, 3 or 4.

In another preferred embodiment, R represents an alkyl group having from 1 to 8 carbons, and x is 0 to 10. The alkyl group can be either straight chain or branched, preferably straight chain. In this embodiment, preferably x is 4-8 and R is $C_1$ to $C_4$ alkyl, preferably methyl or ethyl.

Generally, the concentration of carboxylic acid within the composition used in the process of the invention ranges from about 0.5 wt-% to about 80 wt-%, preferably from about 5 wt-% to about 50 wt-%, and most preferably from about 10 wt-% to about 30 wt-%. Typically the concentration of ester carboxylic acid ranges up to about 15% by weight, although concentrations of up to 50% can be employed in certain embodiments, preferably from about 0.05 to about 15%, and most preferably from about 1% to about 9%.

Hydrogen Peroxide

The reduced-odor compositions of the invention typically also include a hydrogen peroxide constituent. Hydrogen peroxide in combination with the percarboxylic acid provides certain antimicrobial action against microorganisms. Additionally, hydrogen peroxide can provide an effervescent action which can irrigate any surface to which it is applied. Hydrogen peroxide works with a mechanical flushing action once applied which further cleans the surface. An additional advantage of hydrogen peroxide is the food compatibility of this composition upon use and decomposition. For example, combinations of peroxyacetic acid, peroxyoctanoic acid, and hydrogen peroxide result in acetic acid, octanoic acid, water, and oxygen upon decomposition, all of which are food product compatible.

Many oxidizing agents can be used for generating peroxycarboxylic acids. Suitable oxidizing agents, in addition to hydrogen peroxide, include salts of perborate, percarbonate, and persulfate. Hydrogen peroxide is generally preferred for several reasons. After application of the $H_2O_2$/peroxycarboxylic acid germicidal agent, the residue left merely includes water and an acidic constituent. Deposition of these products on the surface of a food product processing apparatus, such as a bath or spray apparatus, will not adversely effect the apparatus, the handling or processing, or the food product washed therein.

Hydrogen peroxide ($H_2O_2$), has a molecular weight of 34.014 and it is a weakly acidic, clear, colorless liquid. The four atoms are covalently bonded in a H—O—O—H structure. Generally, hydrogen peroxide has a melting point of −0.41° C., a boiling point of 150.2° C., a density at 25° C. of 1.4425 grams per cm$^3$, and a viscosity of 1.245 centipoise at 20° C.

Carrier

The reduced-odor composition of or employed in the method of the invention also includes a carrier. The carrier provides a medium which dissolves, suspends, or carries the other components of the reduced-odor composition. For example, the carrier can provide a medium for solubilization and production of peroxycarboxylic acid and for forming an equilibrium mixture. The carrier also functions to deliver and wet the reduced-odor composition of the invention to the food product. To this end, the carrier may contain any component or components that can facilitate these functions.

Polyols are also useful carriers, including polypropylene glycols, polyethylene glycols, sorbitol, and the like. Any of these compounds may be used singly or in combination with other organic or inorganic constituents or, in combination with water or in mixtures thereof.

Generally, the carrier makes up a large portion of the composition and may be the balance of the composition apart from the active antimicrobial components, adjuvants, and the like. Here again, the carrier concentration and type will depend upon the nature of the composition as a whole, the environmental storage, and method of application including concentration of the antimicrobial agent, among other factors. Notably the carrier should be chosen and used at a concentration which does not inhibit the antimicrobial efficacy of the active agent in the composition.

Adjuvants

The reduced-odor composition of or employed in the method of the invention can also include any number of adjuvants. Specifically, the composition can include stabilizing agents, wetting agents, hydrotropes, thickeners, a surfactant, foaming agents, acidifiers, as well as pigments or dyes among any number of constituents which can be added to the composition. Such adjuvants can be preformulated with the reduced-odor composition or added to the system simultaneously, or even after, the addition of the reduced-odor composition. The composition can also contain any number of other constituents as necessitated by the application, which are known to those of skill in the art and which can facilitate the activity of the present invention.

Stabilizing Agents

Stabilizing agents can be added to the composition, for example, to stabilize the peracid and hydrogen peroxide and prevent the premature oxidation of this constituent within the composition.

Chelating agents or sequestrants generally useful as stabilizing agents in the present compositions include alkyl diamine polyacetic acid-type chelating agents such as EDTA (ethylene diamine tetraacetate tetrasodium salt), acrylic and polyacrylic acid-type stabilizing agents, phosphonic acid, and phosphonate-type chelating agents among others. Preferable sequestrants include phosphonic acids and phosphonate salts including 1-hydroxy ethylidene-1,1-diphosphonic acid ($CH_3C(PO_3H_2)_2OH$) (HEDP), amino[tri(methylene phosphonic acid)]([$CH_2PO_3H_2$]$_2$(ethylene diamine[tetra methylene-phosphonic acid)], 2-phosphene butane-1,2,4-tricarboxylic acid, as well as the alkyl metal salts, ammonium salts, or alkyloyl amine salts, such as mono, di, or tetra-ethanolamine salts. The stabilizing agent is used in a concentration ranging from about 0 weight percent to about 20 weight percent of the composition, preferably from about 0.1 weight percent to about 10 weight percent of the composition, and most preferably from about 0.2 weight percent to 5 weight percent of the composition.

Amino phosphates and phosphonates are also suitable for use as chelating agents in the compositions and include ethylene diamine (tetramethylene phosphonates), nitrilotrismethylene phosphates, diethylenetriamine (pentamethylene phosphonates). These amino phosphonates commonly contain alkyl or alkaline groups with less than 8 carbon atoms. The phosphonic acid may also include a low molecular weight phosphonopolycarboxylic acid such as one having about 2-4 carboxylic acid moieties and about 1-3 phosphonic acid groups. Such acids include 1-phosphono-1-methylsuccinic acid, phosphonosuccinic acid and 2-phosphonobutane-1,2,4-tricarboxylic acid.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), (N[$CH_2PO_3H_2$]$_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The above-mentioned phosphonic acids can also be used in the form of water soluble acid salts, particularly the alkali metal salts, such as sodium or potassium; the ammonium salts or the alkylol amine salts where the alkylol has 2 to 3 carbon atoms, such as mono-, di-, or triethanolamine salts. If desired, mixtures of the individual phosphonic acids or their acid salts can also be used.

The concentration of chelating agent useful in the present invention generally ranges from about 0.01 to about 10 wt-%, preferably from about 0.1 to about 5 wt-%, most preferably from about 0.5 to about 2 wt-%.

Wetting or Defoaming Agents

Also useful in the composition are wetting and defoaming agents. Wetting agents function to increase the surface contact or penetration activity of the reduced-odor composition. Wetting agents which can be used in the composition include any of those constituents known within the art to raise the surface activity of the composition.

Along these lines, surfactants, and especially nonionic surfactants, can also be useful in the present invention. Nonionic surfactants which can be useful in the present invention are those which include ethylene oxide moieties, propylene oxide moieties, as well mixtures thereof, and ethylene oxide-propylene oxide moieties in either heteric or block formation. Additionally useful in the present invention are nonionic surfactants which include an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to a alkyl chain where the ethylene oxide and propylene oxide moieties can be in any randomized or ordered pattern and of any specific length. Nonionic surfactants useful in the present invention can also include randomized sections of block and heteric ethylene oxide propylene oxide, or ethylene oxide-propylene oxide, such as ethylene diamine ethylene oxides, ethylene diamine propylene oxides, mixtures thereof, and ethylene diamine EO—PO compounds, including those sold under the tradename Tetronic.

Generally, the concentration of nonionic surfactant used in a composition of the present invention can range from about 0 wt-% to about 5 wt-% of the composition, preferably from about 0 wt-% to about 2 wt-% of the concentrate composition, and most preferably from about 0 wt-% to about 1 wt-% of the composition.

The composition can also contain additional ingredients as necessary to assist in defoaming. Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

Especially preferably, are those antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, preferably from about 0.01 wt-% to 2 wt-%, and most preferably from about 0.01 wt-% to about 1 wt-%.

Hydrotrope

The food product wash composition of the invention or employed in the method of the invention can also include a hydrotrope coupler or solubilizer. Such materials can be used to ensure that the composition remains phase stable and in a single highly active aqueous form. Such hydrotrope solubilizers or couplers can be used at concentrations that maintain phase stability but do not result in unwanted compositional interaction.

Representative classes of hydrotrope solubilizers or coupling agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

Preferred coupling agents for use in the present compositions and methods include n-octane sulfonate and aromatic sulfonates such as an alkyl aryl sulfonate (e.g., sodium xylene sulfonate or naphthalene sulfonate). Many hydrotrope solubilizers independently exhibit some degree of antimicrobial activity at low pH. Such action adds to the efficacy of the invention but is not a primary criterion used in selecting an appropriate solubilizing agent. Since the presence of the peroxycarboxylic acid material in the protonated neutral state provides beneficial biocidal or antimicrobial activity, the coupling agent should be selected not for its independent antimicrobial activity but for its ability to provide effective single phase composition stability in the presence of substantially insoluble peroxycarboxylic acid materials and the more soluble compositions of the invention. Generally, any number of surfactants may be used consistent with the purpose of this constituent.

Anionic surfactants useful with the invention include alkyl carboxylates, linear alkylbenzene sulfonates, paraffin sulfonates and secondary n-alkane sulfonates, sulfosuccinate esters and sulfated linear alcohols.

Zwitterionic or amphoteric surfactants useful with the invention include β-N-alkylaminopropionic acids, n-alkyl-β-iminodipropionic acids, imidazoline carboxylates, n-alky-Il-etaines, amine oxides, sulfobetaines and sultaines.

Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds. Typically, the surfactants useful in the context of this invention are synthetic organic polyoxypropylene (PO)-polyoxyethylene (EO) block copolymers. These surfactants have a diblock polymer including an EO block and a PO block, a center block of polyoxypropylene units (PO), and having blocks of polyoxyethylene grated onto the polyoxypropylene unit or a center block of EO with attached PO blocks. Further, this surfactant can have further blocks of either polyoxyethylene or polyoxypropylene in the molecule. The average molecular weight of useful surfactants ranges from about 1000 to about 40,000 and the weight percent content of ethylene oxide ranges from about 10-80% by weight.

Also useful in the context of this invention are surfactants including alcohol alkoxylates having EO, PO and BO blocks. Straight chain primary aliphatic alcohol alkoxylates can be particularly useful as sheeting agents. Such alkoxylates are also available from several sources including BASF Wyandotte where they are known as "Plurafac" surfactants. A particular group of alcohol alkoxylates found to be useful are those having the general formula $R-(EO)_m-(PO)_n$ wherein m is an integer of about 2-10 and n is an integer from about 2-20. R can be any suitable radical such as a straight chain alkyl group having from about 6-20 carbon atoms.

Other useful nonionic surfactants include capped aliphatic alcohol alkoxylates. These end caps include but are not limited to methyl, ethyl, propyl, butyl, benzyl and chlorine. Useful alcohol alkoxylated include ethylene diamine ethylene oxides, ethylene diamine propylene oxides, mixtures thereof, and ethylene diamine EO—PO compounds, including those sold under the tradename Tetronic. Preferably, such surfactants have a molecular weight of about 400 to 10,000. Capping improves the compatibility between the nonionic and the oxidizers hydrogen peroxide and peroxycarboxylic acid, when formulated into a single composition. Other useful nonionic surfactants are alkylpolyglycosides.

Another useful nonionic surfactant is a fatty acid alkoxylate wherein the surfactant includes a fatty acid moiety with an ester group including a block of EO, a block of PO or a mixed block or heteric group. The molecular weights of such surfactants range from about 400 to about 10,000, a preferred surfactant has an EO content of about 30 to 50 wt-% and wherein the fatty acid moiety contains from about 8 to about 18 carbon atoms.

Similarly, alkyl phenol alkoxylates have also been found useful in the invention. Such surfactants can be made from an alkyl phenol moiety having an alkyl group with 4 to about 18 carbon atoms, can contain an ethylene oxide block, a propylene oxide block or a mixed ethylene oxide, propylene oxide block or heteric polymer moiety. Preferably such surfactants have a molecular weight of about 400 to about 10,000 and have from about 5 to about 20 units of ethylene oxide, propylene oxide or mixtures thereof.

The concentration of hydrotrope useful in the present invention generally ranges from about 0.1 to about 20 wt-%, preferably from about 0.5 to about 10 wt-%, most preferably from about 1 to about 4 wt-%.

Thickening or Gelling Agents

Thickeners useful in the present invention include those which do not leave contaminating residue on the surface of food product or food product processing apparatus. That is, preferred thickeners or gelling agents do not include components incompatible with food or other sensitive products in contact areas.

Generally, thickeners which may be used in the present invention include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. Generally, the concentration of thickener employed in the present compositions or methods will be dictated by the desired viscosity within the final composition. However, as a general guideline, the viscosity of thickener within the present composition ranges from about 0.1 wt-% to about 1.5 wt-%, preferably from about 0.1 wt-% to about 1.0 wt-%, and most preferably from about 0.1 wt-% to about 0.5 wt-%.

Formulation

The compositions of or used in the methods of the invention can be formulated by combining the antimicrobially active materials (e.g., aliphatic carboxylic mono- or di-esters, and hydrogen peroxide) with adjuvant or other components with the materials that form the reduced-odor composition. The compositions can also be formulated with preformed peroxycarboxylic acids. The preferred compositions of the invention can be made by mixing the aliphatic carboxylic mono- or di-esters or mixture thereof with an optional hydrotrope solubilizer or coupler, reacting the mixture with hydrogen peroxide and then adding the balance of required ingredients to provide rinsing and antimicrobial action.

A stable equilibrium mixture is produced containing the carboxylic acid or blend with hydrogen peroxide and allowing the mixture to stand for 1-14 days at 15° C. or more. With this preparatory method, an equilibrium mixture will be formed containing an amount of hydrogen peroxide, unoxidized acid, oxidized or peroxycarboxylic acid and unmodified couplers, solubilizer, or stabilizers.

Use Compositions

The invention contemplates a concentrate composition which is diluted to a use solution prior to application to an object. Primarily for reasons of economics, the concentrate would normally be marketed and an end user would preferably dilute the concentrate with water or an aqueous diluent to a use solution.

The level of active components in the concentrate composition is dependent on the intended dilution factor and the desired activity of the peroxycarboxylic acid compound and the carboxylic acid. Generally, a dilution of about 0.5 to about 20 fluid ounces to about 100 gallons of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 20 ounces of concentrate per 100 gallons of water.

Methods Employing the Reduced-Odor Peroxycarboxylic Acid Compositions

The present invention includes methods employing the reduced-odor peroxycarboxylic acid compositions. Typically, these methods employ the antimicrobial or bleaching activity of the peroxycarboxylic acid. For example, the invention includes a method for reducing a microbial population, a method for reducing the population of a microorganism on skin, a method for treating a disease of skin, a method for reducing an odor, a method for bleaching. These methods can operate on an object, surface, in a body or stream of water or a gas, or the like, by contacting the object, surface, body, or stream with a reduced-odor peroxycarboxylic acid composition of the invention. Contacting can include any of numerous methods for applying a composition, such as spraying the composition, immersing the object in the composition, foam or gel treating the object with the composition, or a combination thereof.

The present reduced-odor compositions can be employed for reducing the population of pathogenic microorganisms, such as pathogens of humans, animals, and the like. The reduced-odor compositions can exhibit activity against pathogens including fungi, molds, bacteria, spores, and viruses, for example, parvovirus, coxsackie virus, herpes virus, S. aureus, E. coli, Streptococci, Legionella, mycobacteria, or the like. Such pathogens can cause a varieties of diseases and disorders, including athletes foot, hairy hoof wart disease, mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface. A filter containing the composition can reduce the population of microorganisms in air and liquids.

A concentrate or use concentration of a reduced-odor peroxycarboxylic acid composition of the present invention can be applied to or brought into contact with an object by any conventional method or apparatus for applying an antimicrobial or cleaning composition to an object. For example, the object can be wiped with, sprayed with, and/or immersed in the reduced-odor composition, or a use composition made from the reduced-odor composition. Contacting can be manual or by machine. Food processing surfaces, food products, food processing or transport waters, and the like can be treated with liquid, gel, aerosol, gas, wax, solid, or powdered reduced-odor compositions according to the invention, or solutions containing these compositions.

Contacting a Food Product with the Reduced-Odor Peroxycarboxylic Acid Compositions The present method and system provide for contacting a food product with a reduced-odor composition employing any method or apparatus suitable for applying a reduced-odor composition. For example, the method and system of the invention can contact the food product with a spray of a reduced-odor composition, by immersion in the reduced-odor composition, by foam or gel treating with the reduced-odor composition, or the like. Contact with a spray, a foam, a gel, or by immersion can be accomplished by a variety of methods known to those of skill in the art for applying antimicrobial agents to food. These same methods can also be adapted to apply the reduced-odor compositions of the invention to other objects.

The present methods require a certain minimal contact time of the composition with food product for occurrence of significant antimicrobial effect. The contact time can vary with concentration of the use composition, method of applying the use composition, temperature of the use composition, amount of soil on the food product, number of microorganisms on the food product, type of antimicrobial agent, or the like. Preferably the exposure time is at least about 5 to about 15 seconds.

A preferred method for washing food product employs a pressure spray including the reduced-odor composition. During application of the spray solution on the food product, the surface of the food product can be moved with mechanical action, preferably agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., preferably about 20 to 60° C. to increase efficacy. The spray reduced-odor composition can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One preferred automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the reduced-odor compositions of the invention. These steam jets can be used in combination with cooling water to ensure that the treatment reaching the food product surface is less than 65° C., preferably less than 60° C. The temperature of the spray on the food product is important to ensure that the food product is not substantially altered (cooked) by the temperature of the spray. The spray pattern can be virtually any useful spray pattern.

Immersing a food product in a liquid reduced-odor composition can be accomplished by any of a variety of methods known to those of skill in the art. For example, the food product can be placed into a tank or bath containing the reduced-odor composition. Alternatively, the food product can be transported or processed in a flume of the reduced-odor composition. The washing solution is preferably agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the reduced-odor composition can be rinsed, drained, or evaporated off the food product.

In another alternative embodiment of the present invention, the food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank foamer or an aspirated wall mounted roamer.

In another alternative embodiment of the present invention, the food product can be treated with a thickened or gelled version of the composition. In the thickened or gelled state the washing solution remains in contact with the food product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

EXAMPLES

Example 1

Embodiments of Reduced Odor Peroxycarboxylic Acid Compositions

Octyldimethylamine oxide was added to a peracid composition containing 15% peroxyacetic acid, 10% hydrogen peroxide, and about 40-45% acetic acid. The octyldimethylamine oxide was added at different levels, corresponding to differing molar ratios of peroxyacetic acid (POAA) to acetic acid (AA) to octyldimethylamine oxide (AO-8). The mixture was then compared for remaining odor. As the table below illustrates, a molar ratio 1 or more AO-8 to 1 POAA exhibited a significant reduction in odor. It was surprising that this reduction occurred even at pH too low for ion pair formation between the AO-8 and POAA, i.e. substantially below the 8.2 pKa of POAA.

Odor reduction was also observed for lauryldimethylamine oxide, at a mole ratio of 1 or greater.

| moles | | | mixture results | |
| --- | --- | --- | --- | --- |
| POAA | AA | AO-8 | pH | odor |
| 1 | 3 | 0 | 1.8 | ouch! |
| 1 | 3 | 1 | 3.3 | vinegar |
| 1 | 3 | 2 | 3.7 | slight vinegar |
| 1 | 3 | 3 | 4.8 | amine oxide |
| 1 | 3 | 4 | 4.8 | amine oxide |
| 1 | 3 | 5 | 5.2 | amine oxide |
| 1 | 3 | 1 | 2.0* | vinegar |
| 0 | 0 | 1 | 7.7 | amine oxide |

*pH adjusted with conc. sulfuric acid

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A method of reducing population of microorganism on an object, comprising:
    contacting the object with a reduced-odor peroxycarboxylic acid composition;
    the composition comprising:
        peroxycarboxylic acid; and
        amine oxide;
        the amine oxide being effective for reducing the odor of the peroxycarboxylic acid;
        wherein the composition comprises 2 to 5 moles of amine oxide per mole of peroxycarboxylic acid.

2. The method of claim 1, wherein the object comprises a food product, a food processing surface, a health care surface, a plant product, a body or stream of water, a body or stream of gas, a hospitality sector surface, an industrial sector surface, an agricultural surface, a veterinary surface, or a combination thereof.

3. The method of claim 1, wherein the object comprises a hard surface.

4. The method of claim 1, wherein the object comprises an air stream.

5. The method of claim 1, wherein the object comprises an elastomer, a plastic, a woven substrate, a non-woven substrate, or a combination thereof.

6. The method of claim 1, wherein contacting comprises spraying the composition, immersing the object in the composition, foam or gel treating the object with the composition, or a combination thereof.

7. The method of claim 1, wherein the amine oxide comprises octyldimethylamine oxide, lauryldimethylamine oxide, or a mixture thereof.

8. The method of claim 1, wherein the amine oxide comprises alkyldimethylamine oxide, dialkylmethylamine oxide, alkyldialkoxylamine oxide, dialkylalkoxyamine oxide, dialkyletheramine oxide and dialkoxyetheramine oxide.

9. The method of claim 1, wherein the amine oxide has a formula of $(R_1R_2R_3)NO$ and wherein $R_1$, $R_2$, and $R_3$ are alkyl groups.

10. The method of claim 9, wherein the $R_1$ alkyl group has about 4 to 18 carbon atoms.

11. The method of claim 9, wherein the $R_1$ alkyl group has about 6 to 8 carbon atoms.

12. The method of claim 11, wherein the $R_2$ and $R_3$ alkyl groups have 1 to 2 carbon atoms.

13. The method of claim 1, wherein the mole ratio of amine oxide to peroxycarboxylic acid is greater than 3.

14. The method of claim 1, wherein the peroxycarboxylic acid comprises peroxyacetic acid and the composition further comprises acetic acid.

15. The method of claim 1, wherein the peroxycarboxylic acid comprises peroxyformic acid, peroxyacetic acid, peroxypropionic acid, peroxybutyric acid, peroxypentanoic acid, or mixture thereof.

16. A method of reducing population of microorganism on an object, comprising:
    contacting the object with a reduced-odor peroxycarboxylic acid composition;
    the composition comprising:
        peroxyacetic acid; and
        octyl dimethyl amine oxide or octyl diethyl amine oxide;
        the amine oxide being effective for reducing the odor of the peroxycarboxylic acid;
        mole ratio of amine oxide to peroxycarboxylic acid being 2 to 5.

* * * * *